(12) United States Patent
Rothberg et al.

(10) Patent No.: US 9,505,030 B2
(45) Date of Patent: Nov. 29, 2016

(54) ULTRASONIC TRANSDUCERS IN COMPLEMENTARY METAL OXIDE SEMICONDUCTOR (CMOS) WAFERS AND RELATED APPARATUS AND METHODS

(71) Applicant: Butterfly Network, Inc., Guilford, CT (US)

(72) Inventors: Jonathan M. Rothberg, Guilford, CT (US); Keith G. Fife, Palo Alto, CA (US); Nevada J. Sanchez, Guilford, CT (US); Susan A. Alie, Stoneham, MA (US)

(73) Assignee: Butterfly Network, Inc., Guilford, CT (US)

( * ) Notice: Subject to any disclaimer, the term of this patent is extended or adjusted under 35 U.S.C. 154(b) by 0 days.

(21) Appl. No.: 14/689,119

(22) Filed: Apr. 17, 2015

(65) Prior Publication Data

US 2015/0298170 A1 Oct. 22, 2015

Related U.S. Application Data

(60) Provisional application No. 61/981,464, filed on Apr. 18, 2014.

(51) Int. Cl.
*B81B 3/00* (2006.01)
*B06B 1/02* (2006.01)
(Continued)

(52) U.S. Cl.
CPC . *B06B 1/02* (2013.01); *A61B 8/00* (2013.01); *B06B 1/0292* (2013.01); *B81B 3/0021* (2013.01); *B81B 7/0006* (2013.01);
(Continued)

(58) Field of Classification Search
CPC ......... A61B 8/00; B06B 1/02; B06B 1/0292; B06B 2201/51; B06B 2201/54; B06B 2201/152; B81B 3/0021; B81B 7/0006; B81B 2201/0271; B81C 1/00158; B81C 1/00246; B81C 2203/0735; H01L 21/32134; H01L 21/56; H01L 21/76838; H01L 23/5226; H01L 23/528; H01L 27/0617; H01L 21/768; H04R 2201/003; H04R 9/18; H04R 11/14
See application file for complete search history.

(56) References Cited

U.S. PATENT DOCUMENTS 5,286,671 A 2/1994 Kurtz et al.
6,430,109 B1 8/2002 Khuri-Yakub et al.
(Continued)

FOREIGN PATENT DOCUMENTS

GB 2 467 776 A 8/2010
KR 10-2013-0134724 A 12/2013
(Continued)

OTHER PUBLICATIONS

International Search Report and Written Opinion mailed Jun. 29, 2015 for Application No. PCT/US2015/026290.
(Continued)

*Primary Examiner* — Galina Yushina
(74) *Attorney, Agent, or Firm* — Wolf, Greenfield & Sacks, P.C.

(57) ABSTRACT

Micromachined ultrasonic transducers formed in complementary metal oxide semiconductor (CMOS) wafers are described, as are methods of fabricating such devices. A metallization layer of a CMOS wafer may be removed by sacrificial release to create a cavity of an ultrasonic transducer. Remaining layers may form a membrane of the ultrasonic transducer.

12 Claims, 7 Drawing Sheets

(51) Int. Cl.
*B81B 7/00* (2006.01)
*B81C 1/00* (2006.01)
*H01L 21/3213* (2006.01)
*H01L 21/56* (2006.01)
*H01L 21/768* (2006.01)
*H01L 21/8238* (2006.01)
*H01L 23/522* (2006.01)
*H01L 23/528* (2006.01)
*H01L 27/06* (2006.01)
*A61B 8/00* (2006.01)
*H01L 27/092* (2006.01)

(52) U.S. Cl.
CPC ....... *B81C1/00158* (2013.01); *B81C 1/00246* (2013.01); *H01L 21/32134* (2013.01); *H01L 21/56* (2013.01); *H01L 21/768* (2013.01); *H01L 21/76838* (2013.01); *H01L 21/823871* (2013.01); *H01L 23/528* (2013.01); *H01L 23/5226* (2013.01); *H01L 27/0617* (2013.01); *H01L 27/0688* (2013.01); *B06B 2201/51* (2013.01); *B81B 2201/0271* (2013.01); *B81C 2203/0735* (2013.01); *B81C 2203/0771* (2013.01); *H01L 27/092* (2013.01); *H01L 2224/16225* (2013.01)

(56) References Cited

U.S. PATENT DOCUMENTS

| | | |
|---|---|---|
| 6,443,901 B1 | 9/2002 | Fraser |
| 6,645,145 B1 | 11/2003 | Dreschel et al. |
| 6,659,954 B2 | 12/2003 | Robinson |
| 6,694,817 B2 | 2/2004 | Degertekin et al. |
| 6,779,387 B2 | 8/2004 | Degertekin |
| 6,795,374 B2 | 9/2004 | Barnes et al. |
| 6,831,394 B2 | 12/2004 | Baumgartner et al. |
| 6,865,140 B2 | 3/2005 | Thomenius et al. |
| 6,958,255 B2 | 10/2005 | Khuri-Yakub et al. |
| 7,030,536 B2 | 4/2006 | Smith et al. |
| 7,037,746 B1 | 5/2006 | Smith et al. |
| 7,052,464 B2 | 5/2006 | Wodnicki |
| 7,104,129 B2 | 9/2006 | Nasiri et al. |
| 7,125,383 B2 | 10/2006 | Hoctor et al. |
| 7,247,246 B2 | 7/2007 | Nasiri et al. |
| 7,250,353 B2 | 7/2007 | Nasiri et al. |
| 7,257,051 B2 | 8/2007 | Thomenius et al. |
| 7,285,897 B2 | 10/2007 | Fisher et al. |
| 7,312,440 B2 | 12/2007 | Degertekin et al. |
| 7,313,053 B2 | 12/2007 | Wodnicki |
| 7,375,420 B2 | 5/2008 | Fisher et al. |
| 7,441,321 B2 | 10/2008 | Baumgartner et al. |
| 7,441,447 B2 | 10/2008 | Degertekin et al. |
| 7,442,570 B2 | 10/2008 | Nasiri et al. |
| 7,451,651 B2 | 11/2008 | Woychik et al. |
| 7,518,251 B2 | 4/2009 | Fisher et al. |
| 7,530,952 B2 | 5/2009 | Huang et al. |
| 7,545,012 B2 | 6/2009 | Smith et al. |
| 7,557,342 B2 | 7/2009 | Federov et al. |
| 7,564,172 B1 | 7/2009 | Huang |
| 7,612,483 B2 | 11/2009 | Degertekin |
| 7,612,635 B2 | 11/2009 | Huang |
| 7,615,834 B2 | 11/2009 | Khuri-Yakub et al. |
| 7,622,848 B2 | 11/2009 | Lee et al. |
| 7,637,149 B2 | 12/2009 | Degertekin et al. |
| 7,646,133 B2 | 1/2010 | Degertekin |
| 7,687,976 B2 | 3/2010 | Haider et al. |
| 7,745,248 B2 | 6/2010 | Park et al. |
| 7,759,839 B2 | 7/2010 | Huang |
| 7,764,003 B2 | 7/2010 | Huang |
| 7,779,696 B2 | 8/2010 | Huang |
| 7,846,102 B2 | 12/2010 | Kupnik et al. |
| 7,878,977 B2 | 2/2011 | Mo et al. |
| 7,880,565 B2 | 2/2011 | Huang |
| 7,888,709 B2 | 2/2011 | Lemmerhirt et al. |
| 7,892,176 B2 | 2/2011 | Wodnicki et al. |
| 7,956,510 B2 | 6/2011 | Huang |
| 8,004,373 B2 | 8/2011 | Huang |
| 8,008,105 B2 | 8/2011 | Huang |
| 8,008,835 B2 | 8/2011 | Degertekin |
| 8,018,301 B2 | 9/2011 | Huang |
| 8,076,821 B2 | 12/2011 | Degertekin |
| 8,105,941 B2 | 1/2012 | Huang |
| 8,120,229 B2 | 2/2012 | Huang |
| 8,203,912 B2 | 6/2012 | Roest et al. |
| 8,222,065 B1 | 7/2012 | Smeys et al. |
| 8,241,931 B1 | 8/2012 | Antoine et al. |
| 8,247,945 B2 | 8/2012 | Huang |
| 8,277,380 B2 | 10/2012 | Daft et al. |
| 8,309,428 B2 | 11/2012 | Lemmerhirt et al. |
| 8,315,125 B2 | 11/2012 | Lemmerhirt |
| 8,327,521 B2 | 12/2012 | Dirksen et al. |
| 8,334,133 B2 | 12/2012 | Federov et al. |
| 8,345,508 B2 | 1/2013 | Wodnicki et al. |
| 8,345,513 B2 | 1/2013 | Huang |
| 8,363,514 B2 | 1/2013 | Huang |
| 8,372,011 B2 | 2/2013 | Degertekin |
| 8,398,554 B2 | 3/2013 | Degertekin |
| 8,399,278 B2 | 3/2013 | Lemmerhirt et al. |
| 8,402,831 B2 | 3/2013 | Kupnik et al. |
| 8,429,808 B2 | 4/2013 | Huang |
| 8,451,693 B2 | 5/2013 | Nikoozadeh et al. |
| 8,483,014 B2 | 7/2013 | Huang |
| 8,526,271 B2 | 9/2013 | Huang |
| 8,559,274 B2 | 10/2013 | Huang |
| 8,563,345 B2 | 10/2013 | Adler et al. |
| 8,647,279 B2 | 2/2014 | Daft et al. |
| 8,658,453 B2 | 2/2014 | Lemmerhirt et al. |
| 8,665,672 B2 | 3/2014 | Soeda et al. |
| 8,957,564 B1 | 2/2015 | Hiroe et al. |
| 9,061,318 B2 | 6/2015 | Rothberg et al. |
| 9,067,779 B1 | 6/2015 | Rothberg et al. |
| 9,242,275 B2 | 1/2016 | Rothberg et al. |
| 2005/0121734 A1 | 6/2005 | Degertekin et al. |
| 2005/0177045 A1 | 8/2005 | Degertekin et al. |
| 2005/0203397 A1 | 9/2005 | Degertekin |
| 2007/0167811 A1 | 7/2007 | Lemmerhirt et al. |
| 2007/0167812 A1 | 7/2007 | Lemmerhirt et al. |
| 2007/0180916 A1 | 8/2007 | Tian et al. |
| 2007/0190680 A1* | 8/2007 | Fukuda ............. B81C 1/0023 438/50 |
| 2007/0215964 A1 | 9/2007 | Khuri-Yakub et al. |
| 2008/0194053 A1 | 8/2008 | Huang |
| 2008/0290756 A1 | 11/2008 | Huang |
| 2008/0294055 A1* | 11/2008 | Adachi ............. B06B 1/0292 600/463 |
| 2008/0296708 A1 | 12/2008 | Wodnicki et al. |
| 2008/0308920 A1 | 12/2008 | Wan |
| 2009/0122651 A1 | 5/2009 | Kupnik et al. |
| 2009/0134497 A1 | 5/2009 | Barth et al. |
| 2009/0148967 A1 | 6/2009 | Wodnicki et al. |
| 2009/0176375 A1 | 7/2009 | Benson et al. |
| 2009/0179287 A1* | 7/2009 | Inaba ................ B81B 3/007 257/415 |
| 2009/0250729 A1* | 10/2009 | Lemmerhirt ........ A61B 8/00 257/254 |
| 2010/0027830 A1 | 2/2010 | Hsu et al. |
| 2010/0225200 A1* | 9/2010 | Kupnik .............. B06B 1/0292 310/300 |
| 2011/0084570 A1 | 4/2011 | Soeda et al. |
| 2011/0115333 A1 | 5/2011 | Ezaki |
| 2011/0140224 A1 | 6/2011 | Kropelnicki et al. |
| 2011/0272693 A1 | 11/2011 | Kobayashi et al. |
| 2011/0316054 A1* | 12/2011 | Fedder .............. B81C 1/00246 257/253 |
| 2012/0074509 A1 | 3/2012 | Berg et al. |
| 2012/0129301 A1 | 5/2012 | Or-Bach et al. |
| 2012/0187508 A1 | 7/2012 | Adler et al. |
| 2012/0248554 A1 | 10/2012 | Klein et al. |
| 2013/0096433 A1 | 4/2013 | Lemmerhirt et al. |
| 2013/0116561 A1 | 5/2013 | Rothberg et al. |
| 2013/0161702 A1 | 6/2013 | Chen |
| 2013/0169110 A1 | 7/2013 | Jeong et al. |
| 2014/0057382 A1 | 2/2014 | Supino et al. |

(56) References Cited

U.S. PATENT DOCUMENTS

| | | |
|---|---|---|
| 2014/0217478 A1 | 8/2014 | Rothberg et al. |
| 2014/0219062 A1 | 8/2014 | Rothberg et al. |
| 2014/0264660 A1 | 9/2014 | Rothberg et al. |
| 2014/0355381 A1* | 12/2014 | Lal .................. B81B 3/0021 367/87 |
| 2015/0084053 A1 | 3/2015 | Rothberg et al. |
| 2015/0251896 A1 | 9/2015 | Rothberg et al. |
| 2016/0009544 A1 | 1/2016 | Rothberg et al. |
| 2016/0009549 A1 | 1/2016 | Rothberg et al. |

FOREIGN PATENT DOCUMENTS

| | | |
|---|---|---|
| WO | WO 2009/107940 A2 | 9/2009 |
| WO | WO 2012/017978 A2 | 2/2012 |
| WO | WO 2014/151525 A2 | 9/2014 |

OTHER PUBLICATIONS

Doody et al., Modeling and Characterization of CMOS-Fabricated Capacitive Micromachined Ultrasound Transducers. J Microelectromech Sys. Feb. 1, 2011;20(1):104-18.

Helin et al., Poly-SiGe-based CMUT array with high acoustical pressure. MEMS. 2012 IEEE 25th International Conference on Micro Electro Mechanical Systems. Jan. 29, 2012;305-8.

Lemmerhirt et al., A 32×32 capacitive micromachined ultrasonic transducer array manufactured in standard CMOS. IEEE Trans Ultrason Ferroelectr Freq Control. Jul. 2012;59(7):1521-36. doi: 10.1109/TUFFC.2012.2352.

Lemmerhirt et al., An electronically-scanned CMUT-in-CMOS transducer for hemodialysis vascular access monitoring. Ultrason Symp. 2011 IEEE International Conference. Oct. 18, 2011;2193-6.

Lu et al., Investigation of thermal stress influence on CMUT in standard CMOS process. Info Auto. 2009 ICIA International Conference. Jun. 22, 2009;1447-51.

Xu et al., Characterization of improved Capacitive Micromachined Ultrasonic Transducers (CMUTS) using ALD high- [Kappa] dielectric isola. MEMS. 2014 IEEE 27th International Conference on Micro Electro Mechanical Systems. Jan. 26, 2014;584-7.

Yu et al., Dual-bottom-electrode CMUT based on standard CMOS process. NEMS. 2001 IEEE International Conference. Feb. 20, 2011;21-4.

International Search Report and Written Opinion mailed Jul. 1, 2014 for Application No. PCT/US2014/014705.

Invitation to Pay Additional Fees mailed Nov. 6, 2014 for Application No. PCT/US2014/025924.

International Search Report and Written Opinion mailed Feb. 18, 2015 for Application No. PCT/US2014/025924.

Office Communication mailed Feb. 13, 2015 for U.S. Appl. No. 14/172,383.

Sil-Via, TSI & Advanced Features. Silex Microsystems. http://www.silexmicrosystems.com/mems-foundry/sil-via-tsi-advanced-features/ [last accessed Jan. 6, 2015]. 4 pages.

Calmes et al., Highly Integrated 2-D Capacitive Micromachined Ultrasonic Transducers. 1999 IEEE Ultrason Symp. 1999;1163-6.

Cheng et al., An Efficient Electrical Addressing Method Using Through-Wafer Vias for Two-Dimensional Ultrasonic Arrays. 2000 IEEE Ultrasonics Symposium. 2000;2:1179-82.

Cheng et al., Electrical Through-Wafer Interconnects with Sub-PicoFarad Parasitic Capacitance. 2001 Microelectromechan Syst Conf. Aug. 24, 2001;18-21.

Daft et al., Microfabricated ultrasonic transducers monolithically integrated with high voltage electronics. Proc Ultrason Symp. 2004;493-6.

Dixon-Warren, Overview of MEMS microphone technologies for consumer applications. MEMS J. Mar. 8, 2011. http://www.memsjournal.com/2011/03/overview-of-mems-microphone-technologies-for-consumer-applications.html [last accessed Feb. 19, 2014]. 10 pages.

Eccardt et al., Micromachined ultrasound transducers with improved coupling factors from a CMOS compatible process. Ultrasonics. Mar. 2000;38:774-80.

Eccardt et al., Surface micromachined ultrasound transducer in CMOS technology. Proc Ultrason Symp. 1996;959-62.

Gurun et al., Front-end CMOS electronics for monolithic integration with CMUT arrays: circuit design and initial experimental results. Proc Ultrason Symp. 2008;390-3.

Kim et al., Design and Test of a Fully Controllable 64×128 2-D CMUT Array Integrated with Reconfigurable Frontend ASICs for Volumetric Ultrasound Imaging. IEEE. International Ultrasonics Symposium Proceedings. Oct. 7-10, 2012;77-80. doi: 10.1109/ULTSYM.2012.0019.

Knight et al., Low Temperature Fabrication of Immersion Capacitive Micromachined Ultrasonic Transducers on Silicon and Dielectric Substrates. IEEE Trans Ultrason Ferroelectr Freq Contr. Oct. 2004;51(10):1324-33.

Kupnik et al., CMUT Fabrication Based on a Thick Buried Oxide Layer. Proc IEEE Ultrason Symp. Oct. 2010;2010:547-550. doi:10.1109/ULTSYM.2010.5935935. Epub Jun. 8, 2012. 10 pages.

Kupnik et al., Wafer-Bonded CMUT Meets CMOS. 2010 CMOS Emerging Technology Workshop. May 21, 2010;1-22.

Lin et al., Packaging of Large and Low-Pitch Size 2D Ultrasonic Transducer Arrays. MEMS Conf. 2010;508-11.

Nikoozadeh et al., Forward-Looking Intracardiac Ultrasound Imaging Using a 1-D CMUT Array Integrated With Custom Front-End Electronics. IEEE Trans Ultrason Ferroelectr Freq Contr. Dec. 2008;55(12):2651-60.

Noble et al., A cost-effective and manufacturable route to the fabrication of high-density 2D micromachined ultrasonic transducer arrays and (CMOS) signal conditioning electronics on the same silicon substrate. Proc Ultrason Symp. 2001;941-5.

Noble et al., Low-temperature micromachined CMUTs with fully-integrated analogue front-end electronics. Proc Ultrason Symp. 2002;1045-50.

Oralkan et al., Volumetric Imaging Using 2D Capacitive Micromachined Ultrasonic Transducer Arrays (CMUTs): Initial Results. 2002 IEEE Ultrason Symp. 2002;1083-6.

Oralkan et al., Volumetric Ultrasound Imaging Using 2-D CMUT Arrays. IEEE Trans Ultrason Ferroelectr Freq Contr. Nov. 2003;50(11):1581-94.

Park et al., Fabrication of Capacitive Micromachined Ultrasonic Transducers via Local Oxidation and Direct Wafer Bonding. J Microelectromechan Syst. Feb. 2011;20(1):95-103.

Torkkeli et al., Capacitative microphone with low-stress polysilicon membrane and high-stress polysilicon backplate. Sensors and Actuators. 2000;85:116-23.

Tsuji et al., Low Temperature Process for CMUT Fabrication with Wafer Bonding Technique. IEEE Intl Ultrason Symp Proc. 2010;551-4.

Um et al., An Analog-Digital-Hybrid Single-Chip RX Beamformer with Non-Uniform Sampling for 2D-CMUT Ultrasound Imaging to Achieve Wide Dynamic Range of Delay and Small Chip Area. IEEE International Solid-State Circuits Conference. Feb. 12, 2014;426-8.

Wodnicki et al., Multi-Row Linear CMUT Array Using CMUTs and Multiplexing Electronics. Proc Ultrason Symp. 2009;2696-9.

Wolfeenbuttel et al., Low-temperature silicon wafer-to-wafer bonding using gold at eutectic temperature. Sensors and Actuators A. 1994;43:223-9.

Wygant et al., Integration of 2D CMUT Arrays with Front-End Electronics for Volumetric Ultrasound Imaging. IEEE Trans Ultrason Ferroelectr Freq Contr. Feb. 2008;55(2):327-42.

Zahorian et al., Single chip CMUT arrays with integrated CMOS electronics: fabrication process development and experimental results. Proc Ultrason Symp. 2008;386-9.

Zhuang et al., Wafer-bonded 2-D CMUT arrays incorporating through-wafer trench-isolated interconnects with a supporting frame. IEEE Trans Ultrason Ferroelectr Freq Control. Jan. 2009;56(1):182-92. doi: 10.1109/TUFFC.2009.1018.

Office Communication mailed May 21, 2015 for U.S. Appl. No. 14/208,351.

Office Communication mailed Apr. 3, 2015 for U.S. Appl. No. 14/561,384.

(56) References Cited

OTHER PUBLICATIONS

Office Communication mailed May 15, 2015 for U.S. Appl. No. 14/635,197.
International Preliminary Report on Patentability mailed Aug. 20, 2015 for Application No. PCT/US2014/014705.
International Preliminary Report on Patentability mailed Sep. 24, 2015 for Application No. PCT/US2014/025924.
International Search Report and Written Opinion mailed Oct. 29, 2015 for Application No. PCT/US2015/040342.
Notice of Allowance mailed Dec. 4, 2015 for U.S. Appl. No. 14/172,383.
Notice of Allowance mailed Sep. 14, 2015 for U.S. Appl. No. 14/208,351.
Notice of Allowance mailed Nov. 10, 2015 for U.S. Appl. No. 14/711,145.
Cha et al., Influences of perforation ratio in characteristics of capacitive micromachined ultrasonic transducers in air. Sensors Actuators A. 2011;171:191-8.
Manzanares et al., Air-coupled MUMPs capacitive micromachined ultrasonic transducers with resonant cavities. Ultrason. 2012;52:482-9.
Zhuang et al., Integration of trench-isolated through-wafer interconnects with 2d capacitive micromachined ultrasonic transducer arrays. Sensors Actuators A. 2007;138:221-9.
PCT/US2014/014705, Aug. 20, 2015, International Preliminary Report on Patentability.
PCT/US2014/025924, Sep. 24, 2015, International Preliminary Report on Patentability.
PCT/US2015/040342, Oct. 29, 2015, International Search Report and Written Opinion.

\* cited by examiner

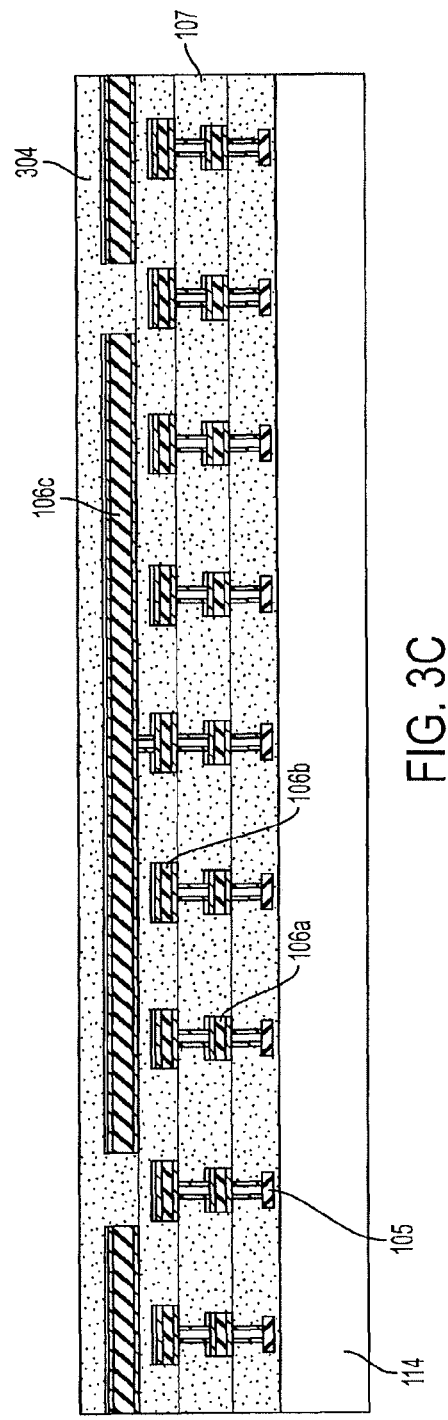
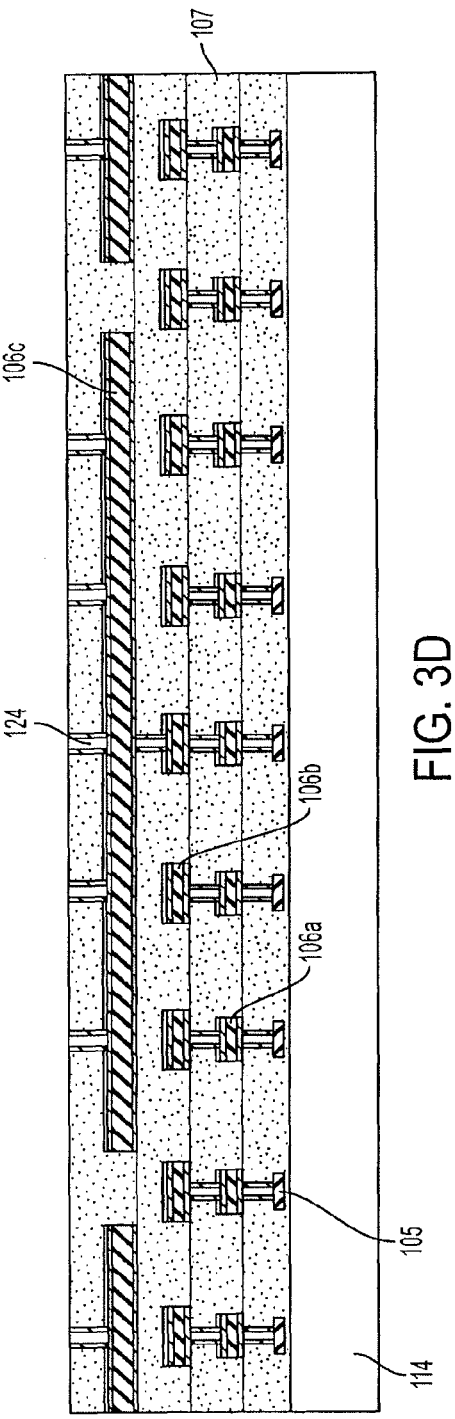

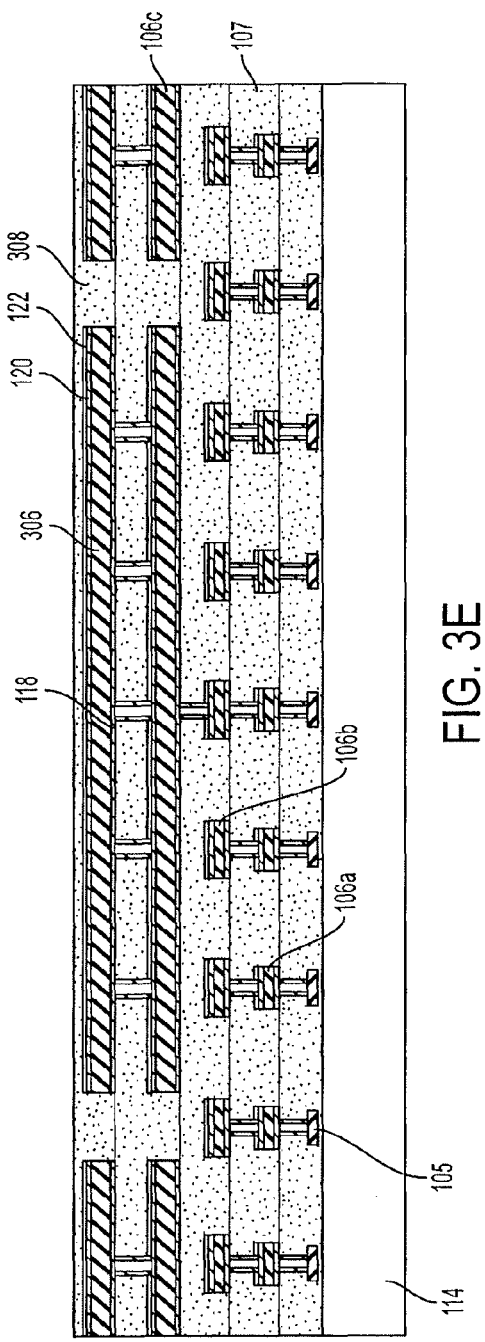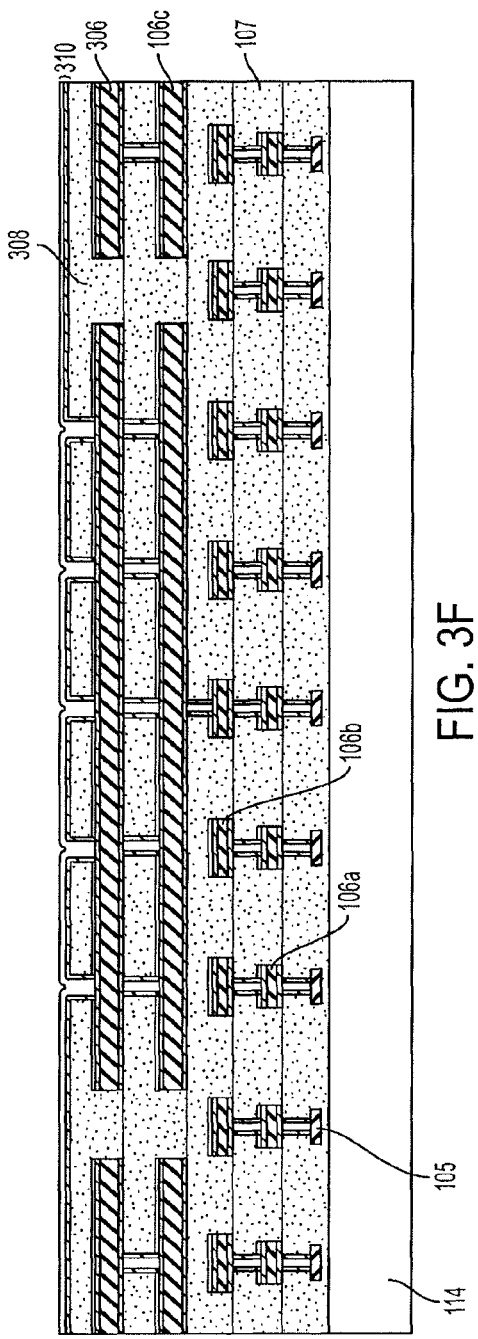

ULTRASONIC TRANSDUCERS IN COMPLEMENTARY METAL OXIDE SEMICONDUCTOR (CMOS) WAFERS AND RELATED APPARATUS AND METHODS

CROSS-REFERENCE TO RELATED APPLICATIONS

The present application claims the benefit under 35 U.S.C. §119(e) of U.S. Provisional Patent Application Ser. No. 61/981,464 entitled "ULTRASONIC TRANSDUCERS IN COMPLEMENTARY METAL OXIDE SEMICONDUCTOR (CMOS) WAFERS AND RELATED APPARATUS AND METHODS," filed Apr. 18, 2014, which is incorporated herein by reference in its entirety.

BACKGROUND

Field

The technology described herein relates to micromachined ultrasonic transducers and related apparatus and methods.

Related Art

Capacitive Micromachined Ultrasonic Transducers (CMUTs) are known devices that include a membrane above a micromachined cavity. The membrane may be used to transduce an acoustic signal into an electric signal, or vice versa. Thus, CMUTs can operate as ultrasonic transducers.

Two types of processes can be used to fabricate CMUTs. Sacrificial layer processes form the membrane of the CMUT on a substrate above a sacrificial layer which is then removed to form the cavity of the CMUT beneath the membrane. Wafer bonding processes bond two wafers together to form a cavity with a membrane.

SUMMARY

Aspects of the present technology provide micromachined ultrasonic transducers (e.g., CMUTs) in complementary metal oxide semiconductor (CMOS) wafers, utilizing a removed metallization of the CMOS wafer as an acoustic cavity for one or more micromachined ultrasonic transducers. Accordingly, the ultrasonic transducers may be integrated with the CMOS wafers and formed in the wafers, avoiding any requirement for wafer bonding to fabricate ultrasonic transducers. Integration of the ultrasonic transducers with the CMOS wafers may therefore be simplified and made more robust compared to if wafer bonding was used. Moreover, use of a removed CMOS metallization layer as the cavity of an ultrasonic transducer may facilitate formation of integrated circuits (ICs) on the CMOS wafer beneath the ultrasonic transducer, thus reducing or minimizing the space on the CMOS wafer needed to form integrated ultrasonic transducers and integrated circuits. As a result, compact complementary metal oxide semiconductor (CMOS) ultrasonic transducers (CUTs) having monolithically integrated ultrasonic transducers and CMOS ICs may be formed in accordance with some embodiments.

According to an aspect of the technology, a complementary metal oxide semiconductor (CMOS) wafer comprises a semiconductor substrate and an ultrasonic transducer. The ultrasonic transducer comprises a cavity representing a removed first metallization layer of the CMOS wafer, an electrode disposed between the cavity and the semiconductor substrate, and an acoustic membrane of the CMOS wafer comprising a dielectric layer and a second metallization layer of the CMOS wafer. The cavity may be disposed between the semiconductor substrate and the acoustic membrane. The CMOS wafer may further comprise integrated circuitry on the semiconductor substrate, coupled to the ultrasonic transducer and configured to control operation of the ultrasonic transducer.

According to an aspect of the present technology, an apparatus comprises an ultrasonic transducer in a complementary metal oxide semiconductor (CMOS) wafer for which a removed portion of a metallization layer defines at least part of an acoustic cavity of the ultrasonic transducer.

According to an aspect of the present technology, a complementary metal oxide semiconductor (CMOS) wafer comprises a semiconductor substrate, a first metallization layer, and an ultrasonic transducer. The ultrasonic transducer comprises a cavity formed in the first metallization layer, an electrode disposed between the cavity and the semiconductor substrate, and an acoustic membrane of the CMOS wafer comprising a dielectric layer and a second metallization layer of the CMOS wafer. The cavity may be disposed between the semiconductor substrate and the acoustic membrane. The CMOS wafer further comprises integrated circuitry on the semiconductor substrate, coupled to the ultrasonic transducer and configured to control operation of the ultrasonic transducer.

According to an aspect of the technology, a method comprises forming an acoustic membrane of an ultrasonic transducer in a complementary metal oxide semiconductor (CMOS) wafer by stacking multiple layers of the CMOS wafer including at least one dielectric layer and a first metallization layer of the CMOS wafer. The method further comprises creating at least one access hole to a second metallization layer of the CMOS wafer, the second metallization layer comprising an inner metal layer bounded by first and second conductive liner layers, which in some embodiments include a metal. The method further comprises forming a cavity in the CMOS wafer by removing at least a portion of the inner metal layer of the first metallization layer through the at least one access hole using a selective etch, thereby releasing the acoustic membrane while substantially retaining the first and second conductive liner layers. The method further comprises sealing the at least one access hole with an insulating material, and coupling the first and second conductive liner layers to integrated circuitry of the CMOS wafer.

According to an aspect of the present application, a method comprises defining at least in part an acoustic cavity of an ultrasonic transducer in a complementary metal oxide semiconductor (CMOS) wafer by removing at least part of a metallization layer of the CMOS wafer.

BRIEF DESCRIPTION OF THE DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

FIGS. 3A-3J illustrate a fabrication sequence for fabricating a CMUT in a CMOS wafer consistent with the process of FIG. 2, according to a non-limiting embodiment of the present application.

DETAILED DESCRIPTION

Figure 1:
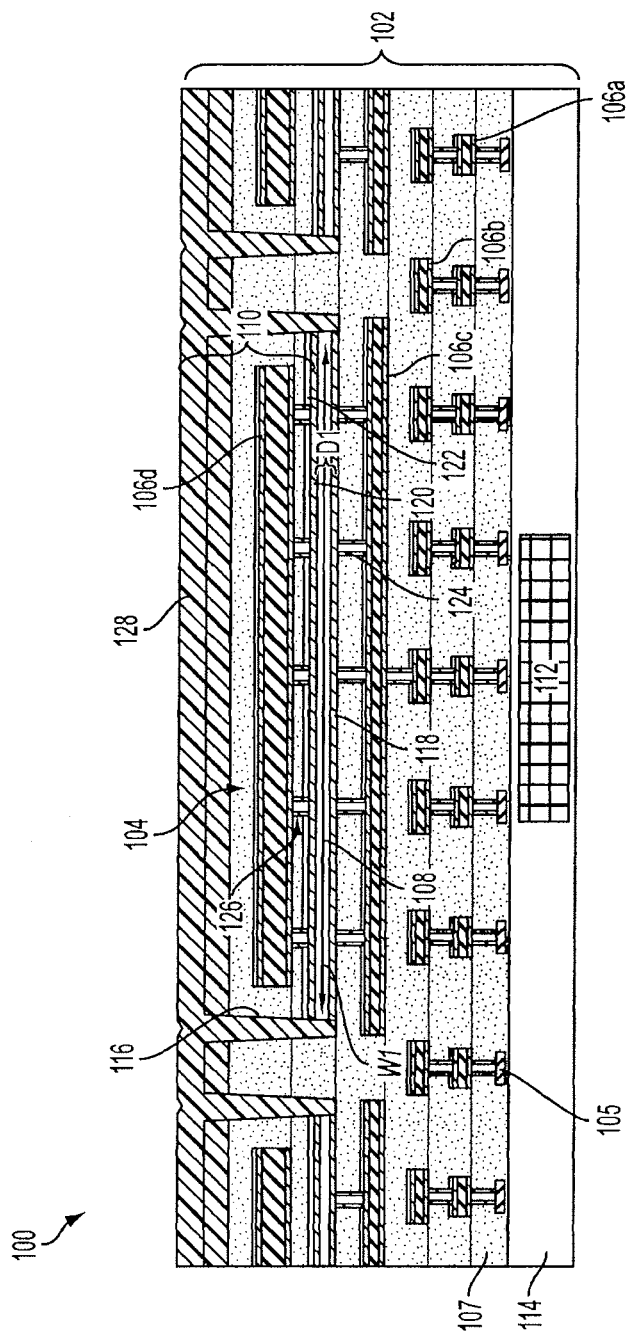
FIG. 1 illustrates a capacitive micromachined ultrasonic transducer (CMUT) formed in a CMOS wafer and integrated with a CMOS IC to form a CUT, according to a non-limiting embodiment of the present application.

Aspects of the present technology arise from Applicants' appreciation that certain feature dimensions of standard CMOS wafers substantially correspond to certain target feature dimensions of ultrasonic transducers for at least some applications, and thus that ultrasonic transducers may be fabricated in CMOS wafers by taking advantage of such correspondence. That is, Applicants have appreciated that at least some metallization layers of CMOS wafers have thicknesses substantially matching target cavity depths of ultrasonic transducers. Applicants have also appreciated that the thickness of layers of a CMOS wafer overlying the metallization layer substantially matches target membrane thicknesses of ultrasonic transducers. Thus, Applicants have appreciated that ultrasonic transducers may be fabricated in (and therefore integrated with) CMOS wafers by utilizing an appropriately dimensioned CMOS metallization layer as a sacrificial layer to be released to define the cavity of the ultrasonic transducer. Such fabrication provides a simple and robust manner of attaining a high degree of integration of an ultrasonic transducer with a CMOS wafer. Thus, aspects of the present application may facilitate formation of ultrasound system-on-a-chip devices having integrated ultrasonic transducers and circuitry.

Moreover, Applicants have appreciated that using a sacrificial CMOS metallization layer having appropriately situated liner layers may further simplify fabrication of an ultrasonic transducer in a CMOS wafer. By removing only the inner metal of the sacrificial CMOS metallization layer, the remaining liner layers may serve as electrodes for the ultrasonic transducer, obviating any need for further processing to create the electrodes. In this sense, the ultrasonic transducer electrodes are already "built in" to the CMOS metallization layer.

Accordingly, aspects of the present technology provide micromachined ultrasonic transducers (e.g., CMUTs) in CMOS wafers, utilizing a removed metallization of the CMOS wafer as an acoustic cavity for one or more micromachined ultrasonic transducers. The metallization may represent a signal line metallization for routing signals on the CMOS wafer, and portions of the metallization layer which do not need to be removed to form an acoustic cavity of an ultrasonic transducer may be retained on the CMOS wafer and configured as a signal line. The metallization layer may have a multi-layer configuration, including an inner metal and one or more liner layers. In some embodiments, the inner metal may be removed to form the acoustic cavity, while the liner layers may be retained and configured as electrodes of the ultrasonic transducer.

According to an aspect of the present technology, a sacrificial release technique is utilized to remove a CMOS metallization layer from a CMOS wafer to create an acoustic cavity of an ultrasonic transducer formed in the CMOS wafer. The metallization targeted with the sacrificial release may have a thickness substantially corresponding to a target depth of the acoustic cavity. In some embodiments, the ultrasonic transducer may be substantially completed prior to the sacrificial release being performed, such that the sacrificial release may complete (or nearly complete) formation of the ultrasonic transducer. Integrated circuitry may optionally be formed in the CMOS wafer beneath the ultrasonic transducer, and in some embodiments may be configured to control operation of the ultrasonic transducer.

The aspects and embodiments described above, as well as additional aspects and embodiments, are described further below. These aspects and/or embodiments may be used individually, all together, or in any combination of two or more, as the application is not limited in this respect.

According to an aspect of the present technology, a CMOS wafer includes one or more ultrasonic transducers formed therein, for which a partially or completely removed metallization layer of the CMOS wafer defines at least in part a cavity of the ultrasonic transducer(s). FIG. 1 illustrates a non-limiting example of such a device.

As shown, the device 100 includes a CMOS wafer 102, with an ultrasonic transducer 104 formed in the CMOS wafer 102. A single ultrasonic transducer 104 is illustrated, but it should be appreciated that aspects of the present application provide for a plurality of ultrasonic transducers in a CMOS wafer, and thus FIG. 1 is a non-limiting illustration. Such a configuration may facilitate formation of an ultrasound system-on-a-chip device or an ultrasound sub-system-on-a-chip device including integrated ultrasonic transducers and circuitry (e.g., analog and/or digital circuitry such as front-end and/or back-end circuitry for controlling operation of the ultrasonic transducers and/or processing signals produced by such transducers, for example to form and/or display ultrasound images). In at least some embodiments, an ultrasound system-on-a-chip device may include, on a single substrate, an arrangement of ultrasonic transducers integrated with analog and digital circuitry, and may be capable of performing ultrasound imaging functions such as emitting and receiving ultrasound waves and processing received ultrasound waves to produce ultrasound images.

The CMOS wafer 102 includes a polysilicon layer 105, a plurality of metallization layers 106a-106d, and a removed metallization layer defining at least in part an acoustic cavity 108 of the ultrasonic transducer 104. A membrane 110 of the ultrasonic transducer 104 is formed of a combination of layers of the CMOS wafer 102 remaining above the cavity 108. Integrated circuitry 112 may be formed in the base layer 114, beneath the ultrasonic transducer 104. The integrated circuitry may be CMOS circuitry and may be integrated with the ultrasonic transducer 104 to form a CUT. In the non-limiting example shown, the integrated circuitry is directly beneath the ultrasonic transducer 104. The polysilicon layer 105 may form part of the integrated circuitry, for instance representing a gate layer for transistors. In some non-limiting embodiments high voltage wiring lines may be disposed above the cavity, but all circuitry may be positioned beneath the ultrasonic transducer.

The CMOS wafer 102 may be any suitable CMOS wafer for the formation of CMOS integrated circuitry and including one or more metallization layers. In the illustrated example, the CMOS wafer 102 includes five metallization layers (metallization layers 106a-106d in addition to the removed metallization layer representing the cavity 108), but other numbers may alternatively be used.

The metallization layers 106a-106d, as well as the removed metallization layer used to form the cavity 108, may be configured as standard CMOS metallization layers for signal routing. Thus, in at least some embodiments they may be substantially planar and may occupy an appropriate portion of a plane within the CMOS wafer for functioning as a signal routing layer. For example, in some embodiments one or more of the metallization layers may occupy substantially an entire plane within the CMOS wafer prior to patterning to define desired signal routing configurations.

Moreover, the metallization layers may be formed of any suitable material(s). For example, aluminum (Al), copper (Cu), or other metals may be used.

In some embodiments, including that illustrated, one or more of the metallization layers may include multiple layers (i.e., a multi-layer configuration), such as an inner metal layer with lower and upper liner (or barrier) layers. In the example of FIG. 1, each of the illustrated metallization layers includes a bottom liner layer (e.g., of titanium nitride (TiN)), a layer of Al, a top liner layer (e.g., of TiN), and a layer of silicon oxynitride (SiON) above the top liner layer to serve as an anti-reflective coating during lithography stages. A multi-layer structure for the metallization which is to be sacrificially removed may be beneficial because the liner layers may be configured and retained as electrodes of the ultrasonic transducer. In this manner, the electrodes of the ultrasonic transducer are formed simply and robustly when initially forming the metallization layer that is to be sacrificially removed. The cavity 108 may be formed by removing only the inner metal layer of the metallization while leaving behind the liner layers. Such selective removal may be achieved using a suitably selective etch process, such as a selective wet etch that is selective for (i.e., etches) the inner metal material of the metallization and which is non-selective for (i.e., does not etch) the material of the liner layers. In this manner, fabrication of the cavity is also simplified in that a timed etch is not needed to obtain the desired cavity dimensions. In some embodiments, the etch may be a hydrofluoric acid (HF) etch, although alternatives are possible.

For example, referring to device 100, the cavity 108 is bounded on the bottom by layer 118 and on the top by layers 120 and 122. The layer 118 may represent a bottom liner layer (e.g., of TiN) of the metallization layer, an internal part of which is partially removed to define the cavity 108. The layer 120 may represent a top liner layer (e.g., of TiN) of the removed metallization layer. The layer 122 may represent an anti-reflective coating of the removed metallization layer. Layers 118 and 120 may be configured as electrodes of the ultrasonic transducer 104. Electric connection to the electrodes (for example by one or more remaining metallization layers of the CMOS wafer) may be made by one or more conductive lines (e.g., vias), such as vias 124 and 126, or in any other suitable manner.

In some embodiments, a multi-layer metallization layer may be configured with an insulating membrane when an inner metal material is removed. For example, the metallization layer may including, in order, TiN-aluminum oxide-Al-aluminum oxide-TiN—SiON, such that when the aluminum is removed an insulating membrane is formed over the TiN electrodes.

In at least some embodiments, the metallization layer that is at least partially removed to form the cavity of an ultrasonic transducer is in fact not completely removed. In this sense, the removal may be local, rather than global. Portions of the metallization layer may be retained to function as signal lines in areas of the CMOS wafer other than where the acoustic cavity is formed, for example to carry signals of various types applicable to the device 100, such as power, control signals, or sensed signals as non-limiting examples. That is, the same CMOS metallization layer may be used in one or more areas of the CMOS wafer as a signal line and may be removed in other areas of the CMOS wafer to define an acoustic cavity of one or more ultrasonic transducers. Such dual functionality is to be distinguished from depositing a metal on a CMOS wafer solely for the purpose of using the metal as a sacrificial layer.

FIG. 1 also illustrates that the CMOS wafer 102 includes suitable dielectric or insulating layers between the metallization layers, such as layers 107. These may be formed of any suitable material (e.g., non-conducting, such as $SiO_2$) and with any suitable thicknesses.

Sealed access holes 116 are also included. One or more access holes may be formed by suitable etching (e.g., a directional etch, such as a reactive ion etch) to access the metallization layer that is removed to form the cavity 108. The metal material of the metallization layer may be removed through the one or more access holes, for example by selective wet etching (e.g., by HF etch). Subsequently, the access holes may be sealed to create a sealed cavity, as shown, which may be a vacuum cavity in some embodiments, although non-vacuum cavities may also be formed. Any suitable sealant material may be used, a non-limiting example of which is $Si_3N_4$.

FIG. 1 illustrates two access holes for the cavity 108. However, it should be appreciated that other numbers (any one or more) may be used. The access holes may be positioned at any suitable location(s) relative to the cavity (e.g., at a periphery as shown, centrally, at both a periphery and a center, etc.) to allow for sufficient removal of the metal material of the metallization layer to create the cavity. Also, holes may optionally be etched and then optionally filled around the borders of the cavity to provide isolation (e.g., acoustic isolation) between transducers or groups of transducers. In such embodiments, the holes may not pass through the membrane 110 but may optionally extend to the cavity 108.

In some embodiments, a plurality of access holes may be positioned suitably to allow removal of the metal material of the metallization layer while also being arranged suitably to allow metal signal connections to run across the chip (e.g., between neighboring ultrasonic transducers). As a specific, but non-limiting, example, a plurality of access holes may be arranged at the periphery of a cavity but there may be enough space between at least two of the access holes to allow metal signal lines to interconnect the metallization layers 106d of neighboring ultrasonic transducers. Considering a top view of such a configuration, the cavity may have a circular shape and the plurality of access holes may be formed around the perimeter in a circle, with metal signal lines running between some of the access holes. Alternatives are possible. For example, the described circular cavity shape may alternatively be rectangular, square, hexagonal, or have any other suitable shape.

The ultrasonic transducer 104 may have any suitable dimensions. The dimensions may be dictated at least in part by an intended application for the transducer, for example to provide desired frequency behavior, desired device size, desired imaging aperture, or other characteristics of interest. Non-limiting examples are provided below.

In some embodiments, the cavity dimensions and/or the membrane thickness of any membrane overlying the cavity may impact the frequency behavior of the membrane, and thus may be selected to provide a desired frequency behavior (e.g., a desired resonance frequency of the membrane). For example, it may be desired in some embodiments to have an ultrasonic transducer with a center resonance frequency of between approximately 20 kHz and approximately 200 MHz, between approximately 1 MHz and approximately 40 MHz, between approximately 1 MHz and approximately 10 MHz, between approximately 2 MHz and approximately 5 MHz, between approximately 5 MHz and approximately 15 MHz, between approximately 10 MHz and approximately 20 MHz, between approximately 20

MHz and approximately 40 MHz, between approximately 50 kHz and approximately 200 kHz, of approximately 2.5 MHz, approximately 4 MHz, any frequency or range of frequencies in between, or any other suitable frequency. For example, it may be desired to use the devices in air, gas, water, or other environments, for example for medical imaging, materials analysis, or for other reasons for which various frequencies of operation may be desired. The dimensions of the cavity and/or membrane may be selected accordingly.

As non-limiting examples, the width W1 of the cavity 108 may be between approximately 5 microns and approximately 500 microns, between approximately 20 microns and approximately 100 microns, may be approximately 30 microns, approximately 40 microns, approximately 50 microns, any width or range of widths in between, or any other suitable width. In some embodiments, the width may be selected to maximize the void fraction, i.e., the amount of area consumed by the cavity compared to the amount of area consumed by surrounding structures. The width dimension may also be used to identify the aperture size of the cavity, and thus the cavities may have apertures of any of the values described above or any other suitable values.

The cavity 108 may have a depth D1, which may be between approximately 0.05 microns and approximately 10 microns, between approximately 0.1 microns and approximately 5 microns, between approximately 0.5 microns and approximately 1.5 microns, any depth or range of depths in between, or any other suitable depth. As previously described, Applicants have appreciated that the thickness of some metallization layers used in standard CMOS wafers may substantially correspond to target depths of the acoustic cavity, and thus the depth of the cavity 108 may be defined at least in part by the thickness of the metallization layer used as the sacrificial layer. For instance, in one embodiment the depth D1 may be approximately ¼ micron, which may substantially correspond to a metallization thickness offered on CMOS wafers.

The membrane 110 may comprise one or more layers and/or structures of the CMOS wafer 102 defining a thickness Tm. In the non-limiting example of FIG. 1, the membrane 110 includes vias (e.g., vias 126), metal layers (e.g., metallization layer 106d), and dielectric or insulating layers (e.g., layers 107). A passivation layer 128 (e.g., formed of $Si_3N_4$) passivates the surface. The thickness Tm (e.g., as measured in the direction generally parallel to the depth D1) may be less than 100 microns, less than 50 microns, less than 40 microns, less than 30 microns, less than 20 microns, less than 10 microns, less than 5 microns, less than 1 micron, less than 0.1 microns, any range of thicknesses in between (e.g., between approximately 1-5 microns, between approximately 1-2 microns, etc.), or any other suitable thickness. The thickness may be selected in some embodiments based on a desired acoustic behavior of the membrane, such as a desired resonance frequency of the membrane. Moreover, Applicants have appreciated that for some standard CMOS wafers, using the metallization layer beneath the top metallization layer as the sacrificial layer for defining the ultrasonic transducer cavity results in the overlying membrane 110 having approximately (and in some cases, substantially) the target thickness for the ultrasonic transducer (e.g., between approximately 1-2 microns). Thus, use of the metallization layer beneath the top metallization layer as the sacrificial layer can significantly simplify fabrication of the ultrasonic transducers in the CMOS wafer.

The thickness Tm may be adjusted by adding/removing material from the upper surface of the membrane. Removal of such material may be accomplished using chemical mechanical polishing (CMP), any form of etching including selective etch, directional etch, wet etch, or laser etch, or any other suitable technique. Furthermore, in some embodiments, the membrane may have a non-uniform thickness, for example being thicker in a center portion over the cavity and thinner above the periphery of the cavity, to form a piston structure. Such structures may provide control over the operating frequency of the ultrasonic transducer.

As a non-limiting example of suitable dimensions of the cavity depth and width and the membrane thickness, in one embodiment the depth D1 may be approximately ¼ micron, the width W1 may be approximately 50 microns, and the thickness Tm of the membrane 110 may be approximately 1-2 microns. Alternatives are possible.

The integrated circuit 112 may be formed in the base layer 114 of the CMOS wafer 102. For example, the base layer 114 may be a bulk silicon layer or other semiconductor substrate, and the integrated circuit 112 may include one or more active silicon circuit elements (e.g., MOS transistors having doped source and drain regions in the silicon), capacitors, resistors, or other circuit components. The integrated circuit 112 may be suitable to operate the ultrasonic transducer 104 in transmit and/or receive modes.

As shown, the ultrasonic transducer 104 may be connected to the IC 112, for example by the illustrated connection of the layer 118 to the via 124. Other manners of making connection are possible.

Figure 2:
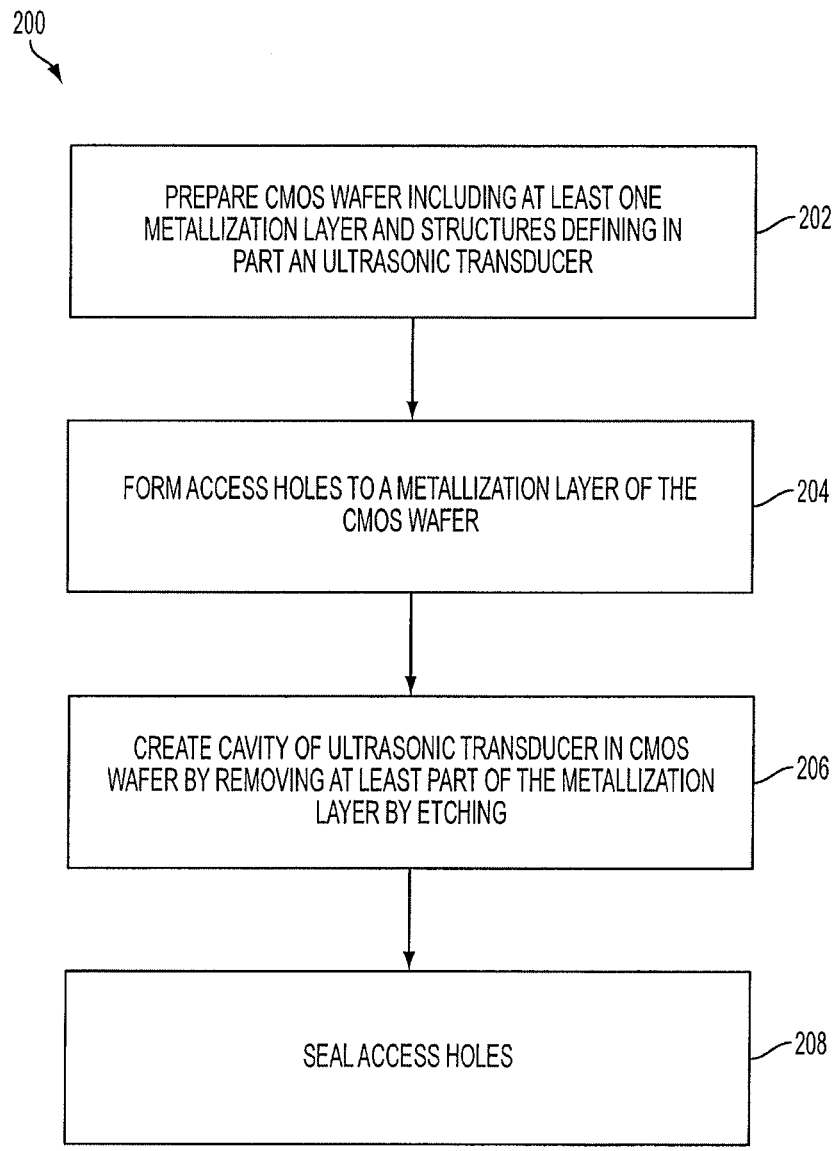
FIG. 2 is a flowchart illustrating a process of fabricating a CMUT in a CMOS wafer, according to a non-limiting embodiment of the present application.

According to an aspect of the present technology, a method of fabricating an ultrasonic transducer in a CMOS wafer is provided, involving removing at least a portion of a metallization layer of the CMOS wafer to create a cavity of the ultrasonic transducer. FIG. 2 is a flowchart illustrating an example of the method.

The method 200 includes, at stage 202, preparation of a CMOS wafer. The CMOS wafer includes at least one metallization layer and structures defining in part an ultrasonic transducer. For example, electrodes and an acoustic membrane may be formed, such as electrodes defined by metallization liner layers and an acoustic membrane of the type represented by acoustic membrane 110 of FIG. 1.

At stage 204 one or more access holes are formed to a metallization layer of the CMOS wafer. As previously described in connection with FIG. 1, the access holes may be created in any suitable manner (e.g., a directional etch) and may be positioned at any suitable location(s) relative to the ultrasonic transducer, including at a periphery and/or center of the area which is to become the cavity of the ultrasonic transducer.

At stage 206, the cavity of the ultrasonic transducer may be created in the CMOS wafer by removing at least part of the metallization layer using a suitable etch technique. For example, a selective etch may be used that is selective for the material (e.g., metal) of the metallization layer to be removed. The removal may be local in some embodiments, but not global. That is, the metallization layer may be removed in the area of the CMOS wafer in which the ultrasonic transducer is located, but may be retained in other areas of the CMOS wafer, for example as a signal line.

At stage 208, the access holes formed in stage 204 may be sealed, to create a sealed ultrasonic transducer cavity. The access holes may be sealed in any suitable manner using any suitable material, such as an insulating material. In some embodiments, a plasma enhanced chemical vapor deposition (PECVD) may be performed to seal the access holes. For example, PECVD $Si_3N_4$ may be used in some embodiments, which may minimize lateral intrusion of the sealing material into the cavity.

The method 200 may be performed at the wafer level, as should be appreciated by the reference to a CMOS wafer throughout FIG. 2. Thus, multiple ultrasonic transducers may be formed in the CMOS wafer, in arrays or other arrangements. One benefit of such a fabrication technique is that large numbers of ultrasonic transducers (e.g., CMUTs) may be formed on a single wafer in a relatively simple, cost-effective manner. Such technology may therefore facilitate fabrication of ultrasound system-on-a-chip devices utilizing arrays (or other arrangements) of micromachined ultrasonic transducers.

It should be appreciated that the stages of method 200 may be performed by different parties in some embodiments. For example, one party in the business of fabricating CMOS wafers may perform stage 202. A second party (e.g., a purchaser of the CMOS wafer) may then perform stages 204, 206, and 208. In other embodiments, a single entity may perform all stages of the method.

Figure 3A:
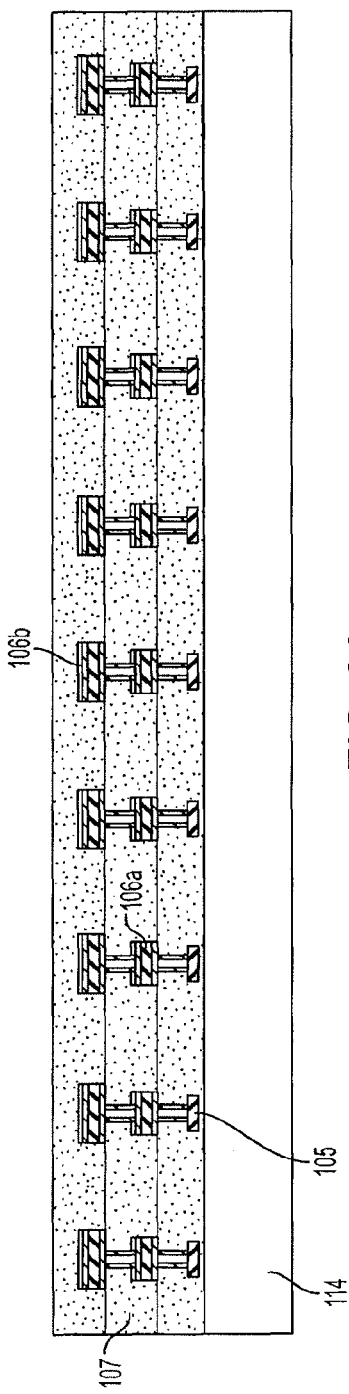

FIGS. 3A-3J illustrate a fabrication sequence for fabricating a CMUT in a CMOS wafer consistent with the process of FIG. 2, according to a non-limiting embodiment of the present application. The starting point for the sequence is shown in FIG. 3A, and includes the base layer 114, patterned polysilicon layer 105, metallization layer 106a, and metallization layer 106b, with layers 107.

Figure 3B:
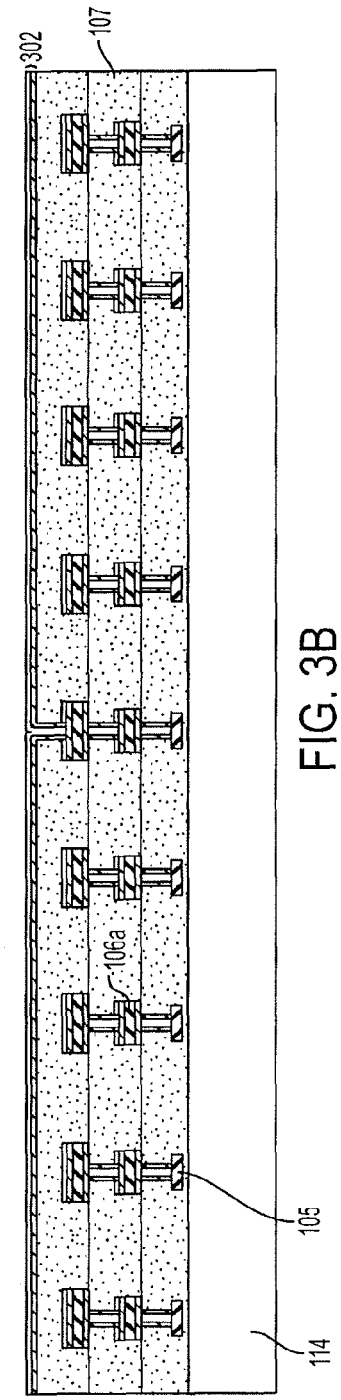

As shown in FIGS. 3B-3D, the via 124 of FIG. 1 (shown completed below in FIG. 3D) may be formed. In anticipation of forming the via, as shown in FIG. 3B, the uppermost layer 107 may be suitably etched and a conductive layer 302 may be deposited. The conductive layer 302 may be formed of a desired via material, such as tungsten (W). A liner material (e.g., TiN) may be deposited prior to the tungsten, and thus the conductive layer 302 may have a multi-layer configuration as shown.

As shown in FIG. 3C, the conductive layer 302 may be planarized (e.g., using CMP), and then metallization layer 106c may be formed and patterned. A dielectric or insulating layer 304 (e.g., $SiO_2$) may be formed over the surface.

As shown in FIG. 3D, the dielectric layer 304 may be patterned to allow formation of vias 124. The vias 124 may be formed of a desired via material, such as tungsten (W). A liner material (e.g., TiN) may be deposited prior to the tungsten, giving rise to the multi-layer features of vias 124 illustrated.

Then, in FIG. 3E, a metallization layer 306 is formed. The metallization layer 306 may represent the sacrificial metallization layer from which the cavity 108 of FIG. 1 (and also shown in FIG. 3I) is to be formed. Thus, the previously described layers 118, 120, and 122 are included. A dielectric or insulating layer (e.g., $SiO_2$) 308 may be formed on the uppermost surface.

Figure 3G:
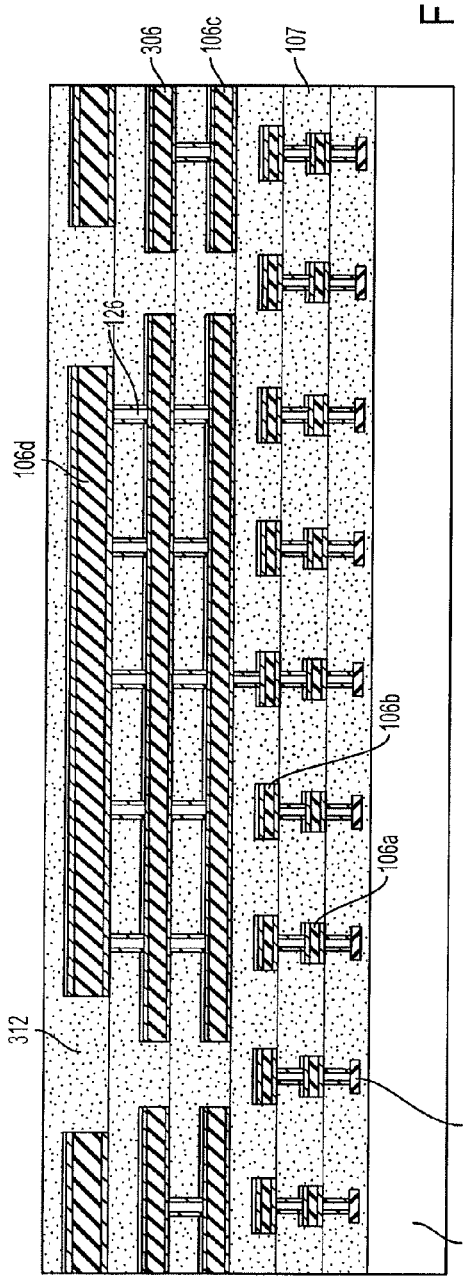

In FIG. 3F the dielectric layer 308 may be patterned and a conductive layer 310 deposited in anticipation of forming vias 126 from FIG. 1 (also shown in FIG. 3G). The conductive layer 310 may be formed of a desired via material, such as tungsten (W). A liner material (e.g., TiN) may be deposited prior to the tungsten, and thus the conductive layer 310 may have a multi-layer configuration as shown.

As shown in FIG. 3G, the conductive layer 310 may be planarized to form vias 126 and metallization layer 106d may be formed and patterned. A dielectric or insulating layer 312 may be formed on the uppermost surface of the structure.

Figure 3H:
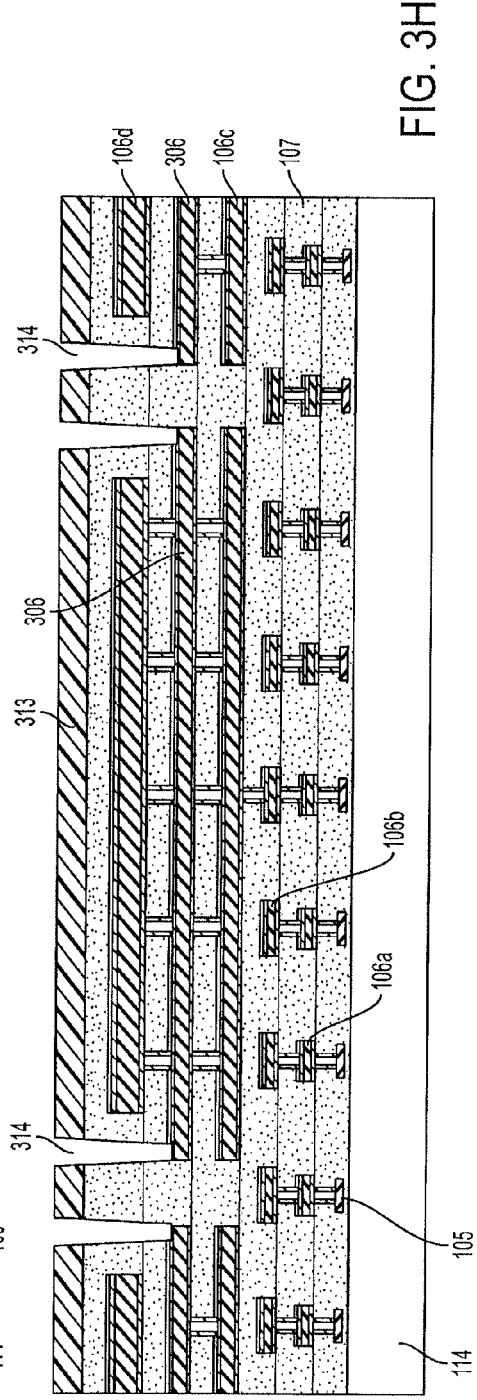

In FIG. 3H a passivation layer (e.g., of $Si_3N_4$) 313 may be formed and access holes 314 may be formed to the metallization layer 306. A suitable etch process may be used to form the access holes.

Figures 3I, 3J:
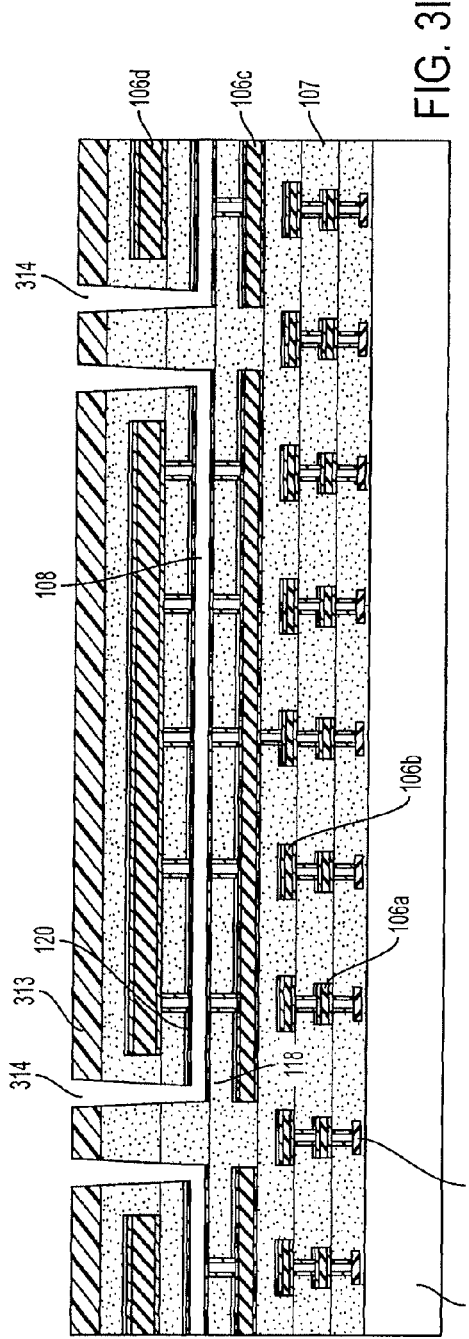

Then, as shown in FIG. 3I, the cavity 108 may be created by removing at least a portion of the metallization layer 306 via the access holes 314. For example, the metallization layer may include an inner metal layer which is selectively etched (for example by wet etch, such as HF etch), leaving behind the layers 118 and 120.

In FIG. 3J the access holes 314 may be sealed with a suitable sealant layer 316. The sealant layer may comprise a passivating material, such as $Si_3N_4$. Other materials are also possible. Thus, the device 100 of FIG. 1 may be achieved through this fabrication sequence.

While FIGS. 3A-3J illustrate a fabrication sequence suitable for use with aluminum metallization layers, it should be appreciated that the various aspects described herein are not limited in this respect. For example, aspects of the present technology may utilize copper metallization layers instead of aluminum. In some embodiments, copper lined with tantalum may be used.

Also, while aspects of the present application have been described as utilizing multi-layer metallization layers of CMOS wafers to define a cavity of an ultrasonic transducer, an alternative may utilize metal-insulator-metal (MIM) layers instead. For example, the insulator of a MIM layer may be removed from between adjacent metal layers in the manner described herein with respect to removing an inner metal material of a metallization layer.

Moreover, according to some embodiments, an ultrasonic transducer may be formed without metal liner layers configured as electrodes adjacent the cavity of the transducer. For example, referring to FIG. 1, in an alternative embodiment the layers 118 and 120 (and also 122) may be omitted, and instead the vias 126 may be disposed suitably to operate in combination as an electrode. For example, the vias 126 may be spaced relative to each other by between approximately 0.1 micron and approximately 0.5 microns (e.g., between approximately 0.2 microns and approximately 0.3 microns). An array of such vias may be operated in combination as an electrode for controlling operation of the ultrasonic transducer. In such embodiments, the vias may have any suitable dimensions, non-limiting examples of which are approximately 0.2 microns×0.2 microns in cross-section, approximately 0.3 microns×0.3 microns in cross-section, or any other suitable dimensions.

Aspects of the present application may be used to build ultrasound devices such as ultrasound probes. The probes may be suitable for imaging a variety of subjects. Ultrasound probes in accordance with some embodiments may include a variety of front-end and/or back-end electronics. In some embodiments, the probes may be ultrasound system-on-a-chip devices.

The aspects of the present application may provide one or more benefits, some of which have been previously described. Now described are some non-limiting examples of such benefits. It should be appreciated that not all aspects and embodiments necessarily provide all of the benefits now described. Further, it should be appreciated that aspects of the present application may provide additional benefits to those now described.

Aspects of the present application provide manufacturing processes suitable for formation of monolithically integrated ultrasonic transducers and CMOS structures (e.g., CMOS ICs). In at least some embodiments, the processes may be simple, robust, relatively inexpensive to perform, and may be scalable to large quantities of ultrasonic transducers. The difficulties associated with wafer bonding, such as poor bond strength, low yield, and the use of high temperature anneals may be avoided. Aspects of the present application provide processes for manufacturing suitably sized ultrasonic transducers for operation in connection with low voltage CMOS ICs. Other benefits may also be provided in accordance with one or more aspects of the present application.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Elements other than those specifically identified by the "and/or" clause may optionally be present, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. A complementary metal oxide semiconductor (CMOS) wafer, comprising:
   a semiconductor substrate;
   an ultrasonic transducer comprising:
   a cavity created by a partial removal of a first metallization layer of the CMOS wafer;
   an electrode disposed between the cavity and the semiconductor substrate; and
   an acoustic membrane comprising a dielectric layer and a second metallization layer of the CMOS wafer, the cavity being disposed between the semiconductor substrate and the acoustic membrane; and
   an integrated circuitry in the semiconductor substrate, coupled to the ultrasonic transducer and configured to control operation of the ultrasonic transducer;
   wherein the electrode disposed between the cavity and the semiconductor substrate is a first electrode of the ultrasonic transducer, and wherein the ultrasonic transducer further comprises a second electrode disposed opposite the first electrode, the second electrode disposed in the acoustic membrane between the cavity and the second metallization layer.

2. The CMOS wafer of claim 1, wherein the electrode disposed between the cavity and the semiconductor substrate comprises a liner layer of the partially removed first metallization layer.

3. The CMOS wafer of claim 1, wherein the acoustic membrane comprises one or more conductive vias.

4. The CMOS wafer of claim 3, wherein at least one of the one or more conductive vias of the acoustic membrane is electrically connected to the second electrode.

5. The CMOS wafer of claim 1, further comprising at least one filled access hole passing through at least part of the acoustic membrane to the cavity.

6. The CMOS wafer of claim 1, comprising a plurality of ultrasonic transducers including the ultrasonic transducer.

7. The CMOS wafer of claim 1, wherein the second metallization layer is embedded within the dielectric layer of the acoustic membrane.

8. The CMOS wafer of claim 1, further comprising at least one hole positioned to not pass through the acoustic membrane.

9. A complementary metal oxide semiconductor (CMOS) wafer, comprising:
   a semiconductor substrate;
   an ultrasonic transducer comprising:
   a cavity created by a partial removal of a first metallization layer of the CMOS wafer;
   an electrode disposed between the cavity and the semiconductor substrate; and
   an acoustic membrane comprising a dielectric layer and a second metallization layer of the CMOS wafer, the cavity being disposed between the semiconductor substrate and the acoustic membrane; and
   an integrated circuitry in the semiconductor substrate, coupled to the ultrasonic transducer and configured to control operation of the ultrasonic transducer;
   wherein the electrode disposed between the cavity and the semiconductor substrate is a bottom electrode of the ultrasonic transducer, and wherein the ultrasonic transducer further comprises a top electrode disposed in the acoustic membrane between the cavity and the second metallization layer, with the cavity being disposed between the bottom electrode and the top electrode, and wherein the bottom and top electrodes comprise liner layers of the partially removed first metallization layer.

10. A complementary metal oxide semiconductor (CMOS) wafer, comprising:
    a semiconductor substrate;
    a first metallization layer; and
    an ultrasonic transducer comprising:
    a cavity formed in the first metallization layer;
    a first electrode disposed between the cavity and the semiconductor substrate, the first electrode comprising a first portion of the first metallization layer; and
    an acoustic membrane comprising a dielectric layer, a second electrode, and a second metallization layer, the cavity being disposed between the semiconductor substrate and the acoustic membrane, the second electrode comprising a second portion of the first metallization layer, and disposed between the cavity and the second metallization layer; and
    integrated circuitry in the semiconductor substrate, coupled to the ultrasonic transducer and configured to control operation of the ultrasonic transducer.

11. The complementary metal oxide semiconductor (CMOS) wafer of claim 10, wherein the first metallization layer is configured to transmit electrical signals in a peripheral area of the substrate.

12. The complementary metal oxide semiconductor (CMOS) wafer of claim 10, wherein the first metallization layer has a plurality of cavities formed therein, and wherein each cavity corresponds to a different ultrasonic transducer.

* * * * *